(12) United States Patent
Stevens et al.

(10) Patent No.: US 8,342,043 B2
(45) Date of Patent: Jan. 1, 2013

(54) SYSTEM FOR COLLECTING A FLUID SAMPLE

(75) Inventors: Jed Stevens, Colorado Springs, CO (US); Gregory Sprenger, Colorado Springs, CO (US); Vitas Sprindys, Taylor, MI (US)

(73) Assignee: Velcon Filters, LLC, Colarado Springs, CO (US)

( * ) Notice: Subject to any disclaimer, the term of this patent is extended or adjusted under 35 U.S.C. 154(b) by 520 days.

(21) Appl. No.: 12/652,433

(22) Filed: Jan. 5, 2010

(65) Prior Publication Data

US 2010/0170350 A1   Jul. 8, 2010

Related U.S. Application Data

(60) Provisional application No. 61/142,500, filed on Jan. 5, 2009.

(51) Int. Cl.
  *G01N 1/14* (2006.01)
  *G01N 1/34* (2006.01)
(52) U.S. Cl. .............. 73/863.23; 73/863.61; 73/864; 73/864.34
(58) Field of Classification Search .. 73/863.23–863.25, 73/863.61, 864, 864.34–864.35, 864.51, 73/864.63
See application file for complete search history.

(56) References Cited

U.S. PATENT DOCUMENTS

| | | | |
|---|---|---|---|
| 3,039,309 A * | 6/1962 | Vesper et al. | 73/863.24 |
| 3,688,191 A * | 8/1972 | Claps | 324/71.1 |
| 4,139,339 A * | 2/1979 | Straitz, III | 431/202 |
| 4,978,506 A * | 12/1990 | Calderwood | 73/863.23 X |
| 5,092,988 A * | 3/1992 | Womack et al. | 73/863.23 X |
| 6,076,410 A * | 6/2000 | Renslow | 73/864.34 |
| 6,726,882 B2 * | 4/2004 | Raisanen | 422/98 |
| 7,132,080 B2 * | 11/2006 | Anderson et al. | 422/501 |
| 7,938,029 B2 * | 5/2011 | Campbell et al. | 73/864.34 |
| 2002/0083781 A1* | 7/2002 | Golner et al. | 73/863.83 |
| 2005/0214408 A1* | 9/2005 | Pilkington et al. | 426/16 |
| 2007/0137935 A1* | 6/2007 | Craig | 184/6.21 |
| 2009/0309619 A1* | 12/2009 | Behle et al. | 324/698 |

FOREIGN PATENT DOCUMENTS

| | | | |
|---|---|---|---|
| DE | 29718049 U1 * | 2/1998 | |
| GB | 2090814 A * | 7/1982 | |
| GB | 2232091 A * | 12/1990 | |
| JP | 57068781 A * | 4/1982 | |
| JP | 60183018 A * | 9/1985 | |
| JP | 03289530 A * | 12/1991 | |
| JP | 04138354 A * | 5/1992 | |

* cited by examiner

*Primary Examiner* — Thomas P Noland
(74) *Attorney, Agent, or Firm* — Fraser Clemens Martin & Miller LLC; James D. Miler

(57) ABSTRACT

A system for collecting a sample of fluid from a fluid source and reintroducing the sample of fluid to the fluid source is disclosed. The system includes a pump in fluid communication with the source of fluid, a filter vessel in fluid communication with the pump and the source of fluid to receive a flow of fluid from the pump and substantially eliminate contaminants from the fluid flowing therethrough, and a fluid reservoir in fluid communication with the pump, wherein the fluid is directed from the pump into the fluid reservoir when in a sample mode.

18 Claims, 1 Drawing Sheet

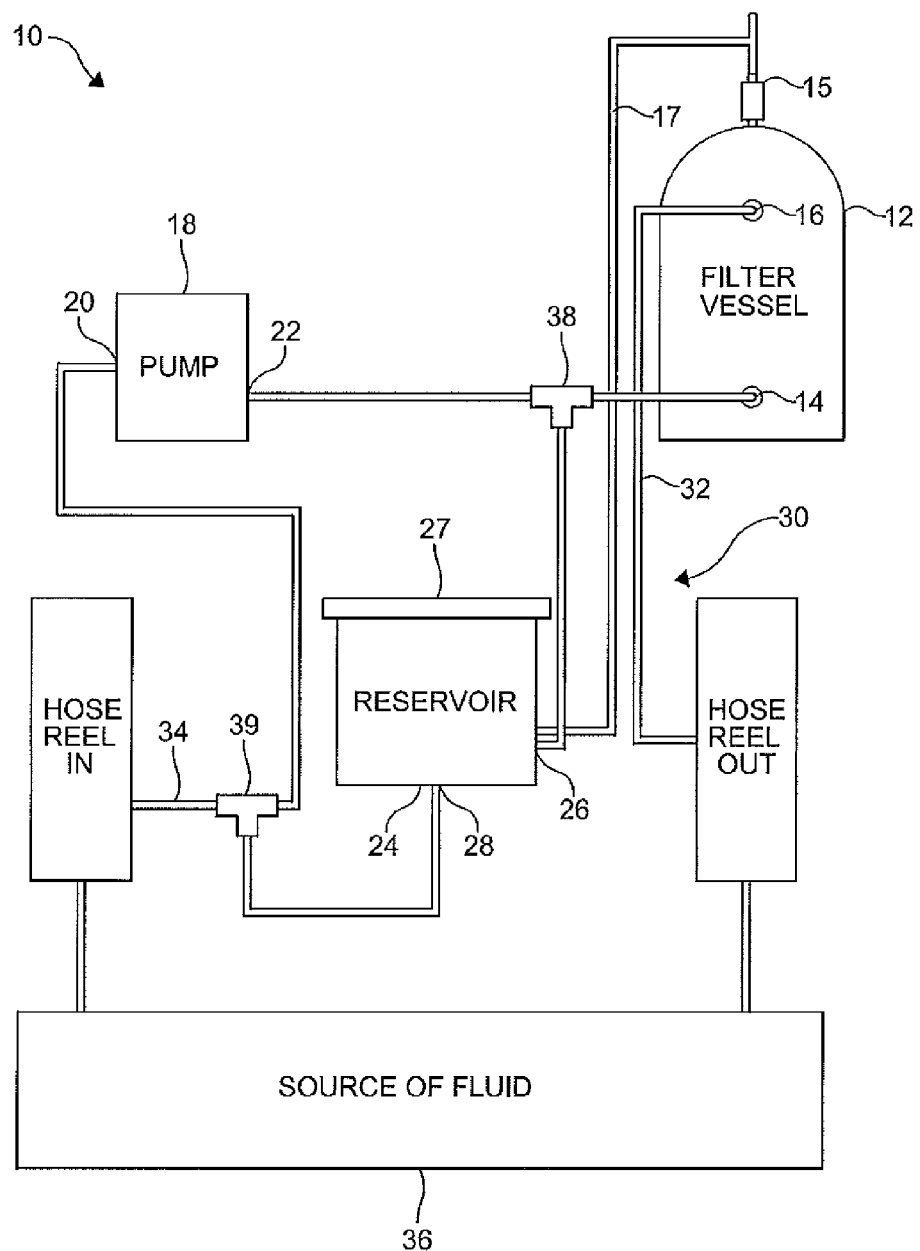

SYSTEM FOR COLLECTING A FLUID SAMPLE

CROSS-REFERENCE TO RELATED APPLICATION

This application claims the benefit of U.S. Provisional Patent Application Ser. No. 61/142,500, filed Jan. 5, 2009, hereby incorporated herein by reference in its entirety.

FIELD OF THE INVENTION

The invention relates to a system for collecting a fluid sample, and more particularly to a system for collecting a test sample of fluid from a source and subsequently reintroducing the sample to the source to minimize a loss of fluid.

BACKGROUND OF THE INVENTION

It is necessary to periodically inspect and test fuel such as aviation fuel to determine whether the fuel has been contaminated. Typically, a sample of fuel is obtained from a source of fuel such as a transient fuel line or a fuel holding tank, for example. The sample of fuel is inspected and tested for contaminates such as water or particulates, for example.

The techniques employed to obtain the sample of fuel for testing typically involve dispensing a quantity of the fuel to be tested into a container. The act of dispensing the sample of fuel from the fueling system into a container is messy, and also allows the introduction of additional contamination such as water from rain, for example. Such a procedure introduces an undesirable source of an error in inspection or testing of the fuel. Additionally, the collected test sample is typically disposed of in a waste tank to prevent an introduction of contaminants to the source of fuel that may have been introduced to the sample.

The disposal of the sample of fuel being tested wastes fuel. In industries such as the aviation industry where frequent and regular testing of fuel is required, the disposal of the sample of fuel amounts to a substantial quantity of fuel being disposed of rather than being consumed in an engine, for example. The disposal of the sample of fuel increases the costs of providing fuel and wastes limited natural petroleum resources.

It would be desirable to produce a system for collecting a sample of fluid from a source and adapted to reintroduce the sample to the source, whereby the risk of introducing contaminants to the source from the sample is minimized.

SUMMARY OF THE INVENTION

The present invention produces a system for collecting a sample of fluid from a source and reintroducing the sample to the source, whereby the risk of introducing contaminants to the source from the sample is minimized, has surprisingly been discovered.

The above objective, as well as others, may be achieved by a system for collecting a fluid from a source of fluid comprising: a pump in fluid communication with the source of fluid; a filter vessel in fluid communication with the pump and the source of fluid to receive a flow of fluid from the pump and substantially eliminate contaminants from the fluid flowing therethrough; and a fluid reservoir in fluid communication with the pump, wherein the fluid is directed from the pump into the fluid reservoir when in a sample mode.

In another embodiment a system for collecting a fluid from a source of fluid comprises: a pump in fluid communication with the source of fluid; a filter vessel in fluid communication with the pump and the source of fluid; and a fluid reservoir in fluid communication with the pump, the filter vessel, and the source of fluid, wherein the fluid is directed from the source through the vessel and back to the source when in a bypass mode, and wherein the fluid is directed from the vessel into the source and into the fluid reservoir when in a sample mode.

In yet another embodiment a system for collecting a fluid from a source of fluid comprises: a pump in fluid communication with the source of fluid; a filter vessel in fluid communication with the pump and the source of fluid; and a fluid reservoir in fluid communication with the pump, the filtering vessel, and the source of fluid, wherein the fluid is directed from the source through the vessel and back to the source when in a bypass mode, wherein the fluid is directed from the pump into the fluid reservoir and the fluid in the filter vessel is directed into the fluid reservoir when in a sample mode, and wherein the fluid is directed from the sample reservoir to the filter vessel when in a sample drain mode to substantially reduce a loss of fluid from the system.

BRIEF DESCRIPTION OF THE DRAWINGS

The above, as well as other objects and advantages of the invention, will become readily apparent to those skilled in the art from reading the following description of an embodiment of the invention when considered in the light of the accompanying drawing which is a schematic illustration of a fluid sampling system according to an embodiment of the invention.

DETAILED DESCRIPTION OF THE PREFERRED EMBODIMENT OF THE INVENTION

The following detailed description and appended drawings describe and illustrate various exemplary embodiments of the invention. The description and drawings serve to enable one skilled in the art to make and use the invention, and are not intended to limit the scope of the invention in any manner.

Referring to drawing, there is illustrated a system, generally indicated by reference numeral 10, for collecting a sample of fluid from a source and reintroducing the sample of fluid to the source. In the illustrated embodiment, the fluid is a fuel such as aviation fuel. However, it should be understood that the system 10 can be employed to sample other fluids. The system 10 includes a filter vessel 12 having an inlet 14, an outlet 16, a fluid pump 18 having an inlet 20 and an outlet 22, and a fluid reservoir 24 having an inlet 26 and an outlet 28. A network of fluid conduits 30 provides fluid communication between the respective inlets 14, 20, 26 and outlets 16, 22, 28 of the filter vessel 12, the pump 18, and the fluid reservoir 24.

The filter vessel 12 may include a vent 15 adapted to provide a flow path for a fluid such as a liquid or a gas out of and into an interior of the vessel 12. The vent 15 allows atmospheric air to enter and exit the filter vessel 12 while fluid is flowing therethrough. Additionally, a fluid conduit 17 forms a fluid communication path between the vent 15 of the filter vessel 12 and the inlet 26 of the fluid reservoir 24. The vent 15, the conduit 17, and the fluid reservoir 24 cooperate to convey the fluid to the fluid reservoir 24 in the event of an overfill condition in the filter vessel 12. Typically, the vent 15 includes a media filter, for example, to prevent contaminants from passing through the vent 15 and entering the filter vessel 12.

The pump 18 is adapted to cause the fluid to flow through the network 30. The pump 18 can be any type of suitable fluid pump such as a piston type pump or an impeller type pump, for example. Typically, the pump is powered by an electrical motor (not shown) in communication with a source of electrical energy (not shown). However, it should be understood that the pump 18 can be powered by other suitable energy sources.

The fluid reservoir 24 includes a removable cover 27 to provide access to an interior thereof for drawing a selected quantity of fluid. Additionally, the cover 27 prevents contaminants from being introduced to the sample of fluid. The fluid reservoir 24 can include other means to access the interior and draw a selected quantity of fluid such as an outlet conduit with a valve, for example. Favorable results have been obtained forming the sample reservoir from a transparent material such as glass or plastic, for example, to facilitate a visual inspection of the fluid contained therein. This allows the fluid to be visually inspected without having to remove the cover 27 and expose the fluid to the environment.

The network 30 includes an outlet conduit 32 providing a flow path for fluid to be discharged from the system 10, and an inlet conduit 34 providing a flow path for fluid to be introduced into the system 10. The outlet conduit 32 and the inlet conduit 34 are in fluid communication with a source of fluid 36. It should be understood that the outlet conduit 32 and the inlet conduit 34 can be provided with suitable fittings to facilitate the attachment to and removal from the source 36. In the illustrated embodiment, the outlet conduit 32 and the inlet conduit 34 each include a hose reel assembly to connect the system 10 to a remote source of fluid.

The network 30 includes three-way actuated valves 38, 39 at selected locations. The valves 38, 39 can be actuated to form a selected fluid flow path through the network 30 and between the respective inlets 14, 20, 26 and outlets 16, 22, 28 of the filter vessel 12, the pump 18, and the fluid reservoir 24. Typically, the valves are manually actuated. However, it should be understood that other means of actuating the valves can be employed such as an electrical actuator, a pneumatic actuator, a hydraulic actuator, and a solenoid actuator, for example.

In certain embodiments, the valves 38, 39 are actuated to provide a first fluid communication path through the network 30 between the outlet 22 of the pump 18 and the inlet 14 of the filter vessel 12; and a second communication path through the network 30 between the source 36 and the inlet 20 of the pump 18.

In operation, the pump 18 is energized to cause fluid to be drawn from the source 36 into the system 10 through the second communication path. Fluid flows through the second fluid communication path into the inlet (or suction side) 20 of the pump 18. Fluid is discharged from the pump 18 through the outlet 22 and flows through the first fluid communication path and inlet 14 of the filter vessel 12. Fluid flows through the filter vessel 12 and exits therefrom through outlet 16. Fluid flows through the second fluid communication path and is reintroduced to the source 36.

The filter vessel 12 substantially eliminates contaminants from the fluid as the fluid flows therethrough. The bypass flow path bypasses the fluid reservoir 24 of the system 10 and removes contaminants from fluid contained in the source 36 and reintroduces the treated fluid to the source 36.

In certain embodiments, the valves 38, 39 are actuated to form the fluid sampling flow path. The valves 38, 39 provide a third fluid communication path between the source 36 and the inlet 20 of the pump 18 and a fourth fluid communication path between the outlet 22 of the pump and the inlet 26 of the fluid reservoir 24.

In operation, the pump 18 is energized to cause fluid to be drawn from the source 36 through the valve 39 and third fluid communication path into the inlet 20 of the pump 18. The fluid is discharged from the pump 18 through the outlet 22 and flows through the fourth fluid communication path through valve 38 into the fluid reservoir 24. Fluid flows from the filter vessel 12 into the fluid source 36. As a non-limiting example, the fluid is received in the fluid reservoir 24 under pressure. Air is introduced into the filter vessel 12 through the vent 15 to replace the fluid being drawn therefrom.

Fluid received in the fluid reservoir 24 can be visually inspected. Favorable results have been obtained by collecting approximately four liters of fluid in the fluid reservoir 24 by causing four liters of fluid to flow from the source 36 into the pump 18 which causes four liters to flow from the pump 18 into the fluid reservoir 24. By obtaining a volume of sample fluid through the extraction of a similar volume of filtered fluid from the source 36, thereby causing the extraction of a similar volume of fluid from the filter vessel 12, replaced by a similar volume of air, the total volume of fluid contained in the source 36 is not substantially altered. Additionally, by providing filtered fluid from the filter vessel 12, a risk of introducing contaminants to the source is minimized.

In certain embodiments, the valves 38, 39 are actuated to form the fluid sample draining flow path. The valves 38, 39 provide a fifth fluid communication path through the network 30 between the outlet 28 of the fluid reservoir 24 and the inlet 20 of the pump 18; and a sixth fluid communication path through the network 30 between the outlet 22 of the pump 18 and the inlet 14 of the filter vessel 12. The fluid conduit 17 provides fluid communication between the vent 15 of the filter vessel 12 and the inlet 26 of the fluid reservoir 24 for transferring excess fuel from the filter vessel 12.

In operation, the pump 18 is energized to cause fluid to be drawn from the fluid reservoir 24 through the outlet 28 into the inlet 20 of the pump 18. The fluid is discharged from the pump 18 through the outlet 22 and the inlet 14 into the filter vessel 12. The fluid sample draining flow path causes the sample of fluid to be drained from the fluid reservoir 24 and received by the filter vessel 12, thus no fuel is lost during the sampling process. The fluid remains in the filter vessel 12 until the valves 38, 39 of the network 30 are actuated to form either the bypass flow path or the fluid sampling flow path, wherein the fluid can be filtered and reintroduced to the source 36.

It should be understood that the system 10 can include a control system (not shown) to control the actuation of the valves 38, 39 and the operation of pump 18. The control system can include components such as solenoid actuators, pressure sensors, flow sensors, and one or more computer processors, for example.

The system provides a substantially fixed network of conduits 30 including the valves 38, 39, wherein a plurality of flow paths can be formed through the network by selectively actuating the valves 38, 39. In particular, the network 30 and the valves 38, 39 are adapted to switch the filter vessel 12 from direct fluid communication with the inlet 20 of the pump 18 to direct fluid communication with the outlet 22 side of the pump 18. The system 10 receives a sample of fluid to be drawn from the source 36, visually inspecting the sample of fluid without exposing the sample to the outside environment, filtering the sample of fluid in the filter vessel 12 to remove contaminants, and reintroduce the filtered sample of fluid to the source 36. Since the sample of fluid is reintroduced to the source 36, the sample does not have to be disposed of and the fluid is preserved for its intended use.

From the foregoing description, one ordinarily skilled in the art can easily ascertain the essential characteristics of this invention and, without departing from the spirit and scope thereof, can make various changes and modifications to the invention to adapt it to various usages and conditions.

What is claimed is:

1. A system for collecting a fluid sample from a source of fluid, the system comprising:
   a pump in fluid communication with the source of fluid;
   a filter vessel in fluid communication with the pump and the source of fluid to receive a flow of fluid from the pump and substantially eliminate contaminants from the fluid flowing therethrough, wherein the filter vessel includes a vent adapted to provide a flow path for a fluid out of and into an interior of the filter vessel; and
   a fluid reservoir in fluid communication with the pump, wherein the fluid is directed from the pump into the fluid reservoir when in a sample mode and the vent is in fluid communication with the fluid reservoir to transfer excess fluid from the filter vessel.

2. The system according to claim 1, wherein the fluid in the filter vessel is directed to the fluid reservoir during the sample mode.

3. The system according to claim 1, wherein air is introduced into the filter vessel through the vent to replace any fluid being drawn therefrom.

4. The system according to claim 1, further comprising at least one valve in fluid communication with at least one of the source of fluid, the pump, the filter vessel, and the fluid reservoir to control a flow of fluid thereto.

5. The system according to claim 1, wherein the fluid reservoir includes a removable cover to provide access to an interior thereof.

6. The system according to claim 1, wherein the fluid reservoir is formed from a transparent material to facilitate a visual inspection of the fluid contained therein.

7. A system for collecting a fluid sample from a source of fluid, the system comprising:
   a pump in fluid communication with the source of fluid;
   a filter vessel in fluid communication with the pump and the source of fluid to receive a flow of fluid from the pump and substantially eliminate contaminants from the fluid flowing therethrough; and
   a fluid reservoir in fluid communication with the pump, wherein the fluid is directed from the pump into the fluid reservoir when in a sample mode and the fluid is directed from the fluid reservoir to the filter vessel when in a sample drain mode to substantially reduce a loss of fluid from the system.

8. A system for collecting a fluid sample from a source of fluid, the system comprising:
   a pump in fluid communication with the source of fluid;
   a filter vessel in fluid communication with the pump and the source of fluid; and
   a fluid reservoir in fluid communication with the pump, the filter vessel, and the source of fluid, wherein the fluid is directed from the source through the vessel and back to the source when in a bypass mode, and wherein the fluid is directed from the vessel into the source and into the fluid reservoir when in a sample mode.

9. The system according to claim 8, wherein the fluid in the filter vessel is directed to the fluid reservoir during the sample mode.

10. The system according to claim 8, wherein the filter vessel includes a vent adapted to provide a flow path for a fluid out of and into an interior of the filter vessel.

11. The system according to claim 10, wherein air is introduced into the filter vessel through the vent to replace any fluid being drawn therefrom.

12. The system according to claim 10, wherein the vent is in fluid communication with the fluid reservoir to transfer excess fluid from the filter vessel.

13. The System according to claim 8, wherein the fluid is directed from the fluid reservoir to the filter vessel when in a sample drain mode to substantially reduce a loss of fluid from the system.

14. The system according to claim 8, further comprising at least one valve in fluid communication with at least one of the source of fluid, the pump, the filter vessel, and the fluid reservoir to control a flow of fluid thereto.

15. The system according to claim 8, wherein the fluid reservoir includes a removable cover to provide access to an interior thereof.

16. The system according to claim 8, wherein the fluid reservoir is formed from a transparent material to facilitate a visual inspection of the fluid contained therein.

17. A system for collecting a fluid sample under pressure from a source of fluid comprising:
   a pump in fluid communication with the source of fluid;
   a filter vessel in fluid communication with the pump and the source of fluid; and
   a fluid reservoir in fluid communication with the pump, the filtering vessel, and the source of fluid, wherein the fluid is directed from the source through the vessel and back to the source when in a bypass mode, wherein the fluid is directed from the pump into the fluid reservoir and the fluid in the filter vessel is directed into the fluid reservoir when in a sample mode, and wherein the fluid is directed from the sample reservoir to the filter vessel when in a sample drain mode to substantially reduce a loss of fluid from the system.

18. The system according to claim 17, wherein the filter vessel includes a vent adapted to provide a flow path for a fluid out of and into an interior of the filter vessel.

* * * * *